United States Patent [19]

Satoh et al.

[11] Patent Number: 5,244,669
[45] Date of Patent: Sep. 14, 1993

[54] FEED ADDITIVES FOR RUMINANTS

[75] Inventors: Hiroyuki Satoh; Takaaki Kobayashi; Takeshi Nagai, all of Kawasaki; Hiroyoshi Okada, Tokyo; Masao Miyake, Yokohama, all of Japan

[73] Assignees: Mitsubishi Kasei Corporation; Ajinomoto Co., Inc., both of Tokyo, Japan

[21] Appl. No.: 731,318

[22] Filed: Jul. 17, 1991

[30] Foreign Application Priority Data

Jul. 20, 1990 [JP] Japan ................... 2-192019

[51] Int. Cl.$^5$ .......................... A23K 1/18; A61K 9/50
[52] U.S. Cl. ...................... 424/438; 424/401; 424/490; 424/494; 424/496; 424/497; 426/96
[58] Field of Search ............... 424/438, 442, 491, 490, 424/498, 502; 426/69, 96

[56] References Cited

U.S. PATENT DOCUMENTS

| | | | |
|---|---|---|---|
| 4,842,863 | 5/1989 | Nishimura et al. | 424/438 |
| 4,876,094 | 10/1989 | Benton | 424/491 |
| 4,976,976 | 12/1990 | Itagaki | 426/69 |
| 4,996,067 | 2/1991 | Kobayashi | 426/96 |

FOREIGN PATENT DOCUMENTS

| | | |
|---|---|---|
| 0268533 | 5/1988 | European Pat. Off. . |
| 2062529 | 7/1971 | Fed. Rep. of Germany . |
| 1692452 | 4/1972 | Fed. Rep. of Germany . |
| 8703173 | 4/1987 | World Int. Prop. O. . |

*Primary Examiner*—Thurman K. Page
*Assistant Examiner*—Sally Gardner
*Attorney, Agent, or Firm*—Oblon, Spivak, McClelland, Maier & Neustadt

[57] ABSTRACT

A feed additive granule for ruminants comprising a granulated physiologically active substance as the core, a first coating layer placed on the surface of said core, said first coating layer containing a high molecular substance which dissolves or swells in water in an acidic pH region of not greater than 5.5 and is stable in a pH region of 5.6 to 8.0, and a second coating layer placed on said first coating layer, said second coating layer being of a substance which is stable in an acidic pH region of not greater than 5.5, dissolves or swells in water in a pH region of 5.6 to 8.0 and is acceptable to ruminants, and some modifications thereof, as well as feed for ruminants comprising such a novel feed additive.

4 Claims, No Drawings

FEED ADDITIVES FOR RUMINANTS

BACKGROUND OF THE INVENTION

Field of the Invention

There are known protected feed additives for ruminants of which the physiologically active substance is prevented as much as possible from being decomposed in the first stomach (i.e., the rumen) and can be digested and absorbed with high efficiency in and at the fourth stomach (i.e., the abomasum) and subsequent digestive tract. Such prior-art protected feed additives for ruminants are, however, decreased in protection when contacted with feed or raw feed material having a lower pH value.

Thus, the present invention relates to feed additives for ruminants. More particularly, the present invention relates to novel feed additives which improve a decrease in protection observed with respect to prior-art protected feed additives for ruminants when contacted with feed or raw feed material having a lower pH value.

Discussion of the Background

A trace amount of feed additives is often formulated into feed for the purpose of supplementing nutrients and/or preventing diseases of live stock.

In the ruminant, however, most of orally administered amino acid, protein and other physiologically active substances are decomposed to ammonia and carbon dioxide gas by microbial fermentation in the rumen wherein the predominant pH is weakly acidic to weakly alkaline. Bacteria and protozoa in the rumen utilize ammonia for their own growth and proliferation. The protein of the microorganisms resulting from growth and proliferation is sent to the strongly acidic abomasum corresponding to the stomach of a single stomach animal, where the protein is partially digested and absorbed. This step of digestion and absorption is completed in the small intestine and absorption is made there so that absorption efficiency is poor.

In order for these physiologically active substances to pass through the rumen without being decomposed by microorganisms and to be efficiently absorbed in the abomasum and subsequent digestive organ, there have been hitherto proposed feed additives for ruminants comprising physiologically active substance(s) coated with a coating material selected from various pH-sensitive materials which are stable in a weakly acidic to weakly alkaline pH region and dissolve or swell at pH 5.5 or less.

When these coated or protected feed additives for ruminants are blended with feeds having a lower pH value such as corn silage (pH of about 4.0), etc., however, the coating layer is dissolved or swollen so that the core material is exposed, whereby the protecting ability of the coating material may no longer be maintained in the rumen.

Furthermore, there have been proposed additives coated with a first coating material containing a pH-sensitive material and then coated with a second coating material of a hydrophobic material such as fat or wax. However, these coated additives are passed through the abomasum and subsequent digestive tract and discharged in the feces as they are so that the coated physiologically active substances might not be effectively utilized. cf., Japanese Patent Application Laid-Open Nos. hei 1-148154 and sho 62-55047.

SUMMARY OF THE INVENTION

Accordingly, as regards protected feed additives proposed in the prior art, an object of the present invention is to develop a method for improving the protecting ability for physiologically active substances when the feed additives are blended with a feed having a lower pH value and for maintaining their utilizability in and after the abomasum.

The present invention thus provides novel feed additives for ruminants which satisfy the above object of the invention and other objects which will become apparent from the description of the invention given hereinbelow.

In some aspects of the present invention, there are provided a feed additive granule for ruminants comprising a granulated physiologically active substance as the core, a first coating layer placed on the surface of said core, said first coating layer containing a high molecular substance which dissolves or swells in water in an acidic pH region of not greater than 5.5 and is stable in a pH region of 5.6 to 8.0, and a second coating layer placed on said first coating layer, said second coating layer being of a substance which is stable in an acidic pH region of not greater than 5.5, dissolves or swells in water in a pH region of 5.6 to 8.0 and is acceptable to ruminants, and some modifications thereof, as well as feed for ruminants comprising such a novel feed additive.

DETAILED DESCRIPTION OF THE INVENTION

As a result of their extensive investigation to solve the problem described above, the present inventors have found that by using as the core material a physiologically active substance to be contained in a feed additive and coating the surface of the physiologically active substance firstly with a high molecular substance which dissolves or swells in water in an acidic pH region of not greater than 5.5 but is stable in a pH region of 5.6 to 8.0 (hereafter referred to as a first coating), granules having an excellent protecting ability in the first stomach and an excellent releasability in the fourth stomach can be obtained and that by further coating the granules with a substance which is stable in an acidic pH region of not greater than 5.5 but dissolves or swells in a pH region of 5.6 to 8.0 and is acceptable to ruminants (hereafter referred to as a second coating), the protecting ability in the first stomach and the releasability in the fourth stomach can be maintained when blended with a feed having a lower pH value such as corn silage, etc. The present invention has been completed on these findings.

The present invention relates to a feed additive for ruminants comprising as the core a physiologically active substance such as amino acid, the surface of said physiologically active substance being subjected to a first coating with a high molecular substance which dissolves or swells in water in an acidic pH region of not greater than 5.5 but is stable in a pH region of 5.6 to 8.0 and the outside of the granules being subjected to a second coating with a substance which is stable in an acidic pH region of not greater than 5.5 but dissolves or swells in water in a pH region of 5.6 to 8.0 and is acceptable to ruminants.

As a second embodiment of the second coating, there can be adopted a method which comprises forming a mass (ball-like, cube-like, etc.) with a substance used for the second coating described above, in which a large number of the first coating particles are incorporated.

Core Materials

The physiologically active substances used for the present invention include nutrients, feeds containing the same, or medicines. Preferred examples include one selected from amino acids, amino acid derivatives, hydroxy homologues of amino acids, proteins, carbohydrates, oils and fats, fatty acids, minerals, vitamins and veterinary medicines, or a mixture of two or more thereof.

Specific examples are amino acids such as lysine, methionine, leucine, isoleucine, valine, cystine, tryptophan, threonine, phenylalanine, arginine, histidine, hydroxylysine, ornithine, alanine, glycine, serine, glutamine, etc.; amino acid derivatives such as N-acylamino acids, N-hydroxymethylmethinone calcium salt, lysine hydrochloride, etc.; hydroxy homologues of amino acids such as 2-hydroxy-4-methylmercaptobutyric acid and salts thereof, etc.; powders of natural nutrients such as cereal powders, feather powders, fish powders, etc.; proteins such as casein, corn protein, potato protein, etc.; carbohydrates such as starch, sucrose, glucose, etc.; vegetable oils and fats such as corn oil, soybean oil, rape seed oil, etc., animal oils and fats such as tallow, lard, etc., and fatty acids such as linoleic acid, etc. and mineral salts thereof; vitamins and substances having functions similar thereto such as vitamin A, vitamin A acetate, vitamin A palmitate, vitamin B's, thiamine, thiamine hydrochloride, riboflavin, nicotinic acid, nicotinamide, calcium pantothenate, choline pantothenate, pyridoxine hydrochloride, choline chloride, cyanocobalamine, biotin, folic acid, p-aminobenzoic acid, vitamin $D_2$, vitamin $D_3$, $\beta$-carotene, vitamin E, etc.; antibiotics of tetracycline type, amino glycoside type, macrolide type and polyether type; insecticides and purgatives such as Negfon, piperazine, etc.; hormones such as estrogene, stilbesterol, hexesterol, thyroprotein, goitrogene, etc.

Granulation of Core Materials

The core materials described above are granulated by well known techniques for granulation, e.g., extrusion granulation, flow granulation, rolling granulation, stirring granulation, etc., prior to the first coating treatment.

Upon granulation, it is advantageous to use substances biologically acceptable to ruminants as feed additives, as a binder for granulation, a vehicle, a disintegrator, a filler for controlling specific gravity, etc.

Examples of the binder include polyvinylpyrrolidone, hydroxypropyl cellulose, polyvinyl alcohol, gum arabic, guar gum, sodium alginate, sodium cellulose glycolate, sodium polyacrylate, etc. As the vehicle, there may be used lactose, mannitol, etc. Usually, these substances are preferably used in an amount of 1 to 50 parts by weight per 100 parts by weight of the core material. They are used in the form of a solution in water and/or alcohol by spraying.

Examples of the disintegrator include potato starch, corn starch, calcium carboxymethylcellulose, sodium carboxymethylcellulose, crystalline cellulose, etc.

As the filler, there may be mentioned minute hollow sodium silicate spheres, minute hollow sodium borosilicate spheres, minute hollow calcium silicate spheres and Shirasu balloon which have a specific gravity of 1.0 or less, and inorganic materials such as talc, kaoline, mica, silica, calcium silicate, diatomaceous earth, etc. which have a specific gravity of 2.0 or more. Using fillers having a specific gravity of 1.0 or less and fillers having a specific gravity of 2.0 or more in an appropriate proportion, a specific gravity of the final granules is chosen to be as close as the specific gravity of the rumen fluid. It is thus prevented to overly prolong a retention time of the feed additive in the rumen.

Additionally, there may be used, if necessary, known additives such as binders, vehicles, disintegrators, lubricants, coloring agents, seasonings, flavors, etc., as disclosed in a Japanese book "YAKUZAI SEIZOHO (JO) IYAKUHIN KAIHATSU KISO KOZA XI", PP.133~154, published in 1971 by CHIJIN SHOKAN.

Furthermore, as is disclosed in U.S. Pat. No. 4,996,067, an intermediate layer containing at least one substance selected from the group consisting of neutral to weakly acidic organic substances, fine powder of neutral inorganic substances and non-ionic hydrophilic high molecular substances can advantageously be placed between the surface of core material granules, i.e., physiologically active substance granules, and a first coating layer of a high molecular substance which dissolves or swells in water in an acidic pH region of not greater than 5.5 and is stable in a pH region of 5.6 to 8.0.

First Coating

For the present invention, it is just sufficient that the outside of the granulated physiologically active substance (core material) is coated with a first coating layer. In this regard, feed additives for ruminants comprising granules composed of a physiologically active substance as the core material, the surface of which is coated with a material containing a high molecular substance which dissolves or swells in water in an acidic pH region of not greater than 5.5 but is stable in a weakly acidic to weakly alkaline pH region, are per se known. Hence, the prior-art techniques can be applied to form the first coating as they are.

In greater detail, examples are as follows;

The first coating is to protect the granules to be in a stable state when the granules are retained in the rumen for a long period of time and, at the same time, to dissolve the core material quickly in the abomasum during a relatively short retention period of time. Accordingly, as a coating material for the first coating, there can be used a synthetic high molecular substance which is stable under weakly acidic to weakly alkaline conditions corresponding to the rumen fluid of a ruminant, namely, in a pH region of 5.6 to 8.0, but disintegrates, swells or dissolves out under strongly acidic conditions corresponding to the gastric juice of the abomasum, namely, dissolves or swells in water in an acidic pH region of 5.5 or less.

Specific examples of the first coating material include the following substances;

Cellulose derivatives such as benzylaminomethyl cellulose, dimethylaminomethyl cellulose, diethylaminomethyl cellulose, piperidylethylhydroxyethyl cellulose, cellulose acetate diethylaminoacetate, cellulose acetate dibutylaminohydroxypropyl ether, ethyl cellulose-N,N-diethylaminohydroxypropyl ether, ethyl cellulose pyridinohydroxypropyl ether, etc.; acetate derivatives such as N,N-diethylvinylamine/vinyl acetate copolymer, vinylpiperizine/vinyl acetate copolymer, vinylbenzylamine/vinyl acetate copolymer, polyvinyldiethylaminoacetoacetal, polyvinylbenzylaminoacetoacetal, vinylpiperidylacetoacetal/vinyl acetate copolymer, polyvinylacetal diethylaminoacetate, etc.; polydiethylaminomethylstyrene, polydietanolaminomethylstyrene, etc.; polydimethylaminoethyl methacrylate, dimethylaminoethylacrylate/methyl methacrylate copolymer, dimethylaminoethyl methacrylate/methyl methacrylate copolymer, 2-(4-morpholino)ethylacrylate/methyl methacrylate copolymer, etc.; polyvinylpyridines such as poly 2-methyl-5-vinylpyridine, poly 2-ethyl-5-vinylpyridine, poly 2-vinylpyridine, poly 4-vinylpyridine, etc.; vinylpyridine/styrene copolymers such as 2-vinylpyridine/styrene copolymer, 4-vinylpyridine/styrene copolymer, 2-ethyl-5-vinylpyridine/styrene copolymer, 2-methyl-5-vinylpyridine/styrene copolymer, etc.; vinylpyridine/acrylonitrile copolymers such as 2-vinylpyridine/acrylonitrile copolymer, 2-ethyl-5-vinylpyridine/acrylonitrile copolymer, vinylethylpyridine/acrylonitrile copolymer, etc.; vinylpyridine/methyl methacrylate copolymers such as 2-vinylpyridine/methyl methacrylate copolymer, 4-vinylpyridine/methyl methacrylate copolymer, etc.; vinylpyridine/butadiene copolymers such as 2-vinylpyridine/butadiene copolymer, etc.; copolymers of 2-vinylpyridine with butadiene and styrene or styrene and methyl methacrylate such as 2-vinylpyridine/styrene/methyl methacrylate copolymer, etc.; copolymers of acrylamide or methacrylamide with acrylonitrile or styrene such as N,N-dimethylaminopropylacrylamide/acrylonitrile copolymer, N,N-dimethylaminopropylacrylamide/styrene copolymer, N,N-dimethylaminopropylmethacrylamide/acrylonitrile copolymer, N,N-dimethylaminopropylmethacrylamide/styrene copolymer, etc.; condensation reaction product of terephthalic acid or maleic acid with N-n-butyldiethanolamine, and benzylamine adduct of propylene glycol/maleic acid polyester.

Of the foregoing first coating materials, preferred ones are synthetic high molecular substances containing amino group(s) and synthetic high molecular substances containing a basic nitrogen. Specific examples include copolymers of dimethylaminoethyl methacrylate with an alkyl methacrylate or alkyl acrylate; copolymers of a vinylpyridine selected from 2-methyl-5-vinylpyridine, 2-vinylpyridine, 4-vinylpyridine, 2-vinyl-6-methylpyridine and 2-vinyl-5-methylpyridine with an acryl compound selected from alkyl methacrylates, alkyl acrylates and acrylonitrile or styrene.

Fusion prevention agents such as talc, aluminum, mica, silica, kaolin, bentonite, diatomaceous earth, stearic acid, aluminum stearate, magnesium stearate, etc. may also be incorporated, together with the first coating materials described above.

The first coating materials may be used in such an amount that the core material is protected to be in a stable state while the coated granules are retained in the rumen of a ruminant, and on the other hand the core material is rapidly dissolved out in the abomasum in a relatively short retention time. The amount varies depending upon the granule size and kind of the first coating material, and is generally 10 to 200 wt % based on the granule (core material) prior to the first coating.

For the first coating, any of general coating techniques such as pan coating, flow coating, centrifugal flow coating, etc. may be adopted.

Upon the first coating, the coating material is usually used in the form of solution in a suitable solvent, e.g., methylene chloride, chloroform, methanol, ethanol, isopropanol, ethyl acetate, acetone, methyl ethyl ketone, toluene, etc. The coating agent may also be used in the form of an emulsion using an emulsifying agent. Upon the coating, the aforesaid fusion prevention agent may also be used in the form of its suspension, in combination.

The thus obtained granules which have been subjected to the first coating should be of a size suited for oral administration to ruminants, and their diameter is of 0.4 to 5 mm, preferably about 0.8 to about 3.5 mm. Feed additives having a specific gravity of about 1 to about 1.4 is preferred since such specific gravity is very similar to that of the rumen fluid of ruminants and there is no danger that a retention time of the feed additives in the rumen is excessively prolonged.

Second Coating and Mass in the Form of Sphere, Cube, etc.

According to the present invention, granules with the first coating layer are then subjected to a second coating with a substance which dissolves or swells in water in a pH range of 5.6 to 8.0 but is stable in an acidic pH region of not greater than 5.5, and is acceptable to a ruminant.

Granules with the first coating layer (i.e., first-coated granules) may be coated uniformly and individually, i.e., separately from each other, with a second coating material.

The second coating may be carried out, as follows; A number of first-coated granules are incorporated into and dispersed within a mass of a spherical, cubic or any other shape composed of a substance for the second coating material above-described thereby to prevent contact with feeds having a lower pH value such as corn silage of the first coating layer comprising a material containing a synthetic high molecular substance which dissolves or swells in water in an acidic pH region of 5.5 or less. As the result, there is no chance that the first coating layer dissolves or swells to expose the core material when a thus prepared feed additive is blended with a feed having a lower pH value. Furthermore, a pH region of 5.6 to 8.0 is a region corresponding to the pH of the rumen fluid in the rumen of a ruminant and hence, the second coating is completely removed or swells in the rumen to allow invasion of the rumen fluid or water so that dissolution of the core material in the abomasum is not prevented. Therefore, the feed additives for ruminants of the present invention can maintain good protecting ability in the rumen and can achieve satisfactory release in the abomasum.

Examples of materials for the second coating or the mass to contain first-coated granules and of a spherical, cubic or any other shape include cereals, beans and potatoes such as corn, milo, wheat, barley, rice, soybean (soybean powder), lupine, sweet potato (dry), cassava, etc., all ground; vegetable oil lees such as soybean cake, cotton seed cake, rape cake, sesame cake, sun flower cake, safflower cake, palm cake, etc.; brans such as rice bran, wheat bran, barley bran, etc.; processed lees such as hominy feed, corn gluten feed, corn germ meal, starch lees, potato protein, beat pulp, beer lees, Japanese sake lees, glutamic acid fermentation lees, konjak Tobiko (ground konjak powders which are air-blown components of konjak), etc.; feeds obtained from animal such as fish powder, meat meal, meat bone meal, blood powder, feather meal, skimmed milk, dried whey, prawn meal, krill meal, casein, gelatin, etc.; yeasts; sugars such as corn starch, dextrin, etc.; vegetable protein such as various leaf meals, soybean protein, wheat gluten, corn zein, etc.; crystalline cellulose; and inorganic fine powders such as talc, silica, white mica, etc.; various vitamins, etc. These materials can be used singly or as admixture of two or more.

A substance to form a second coating or to be the mass to contain first-coated granules is desirably used in amounts of 2 parts by weight or more based on 100 parts by weight of the first-coated granules. There is no critical upper limits to such amounts, but amounts of 2 to 200 parts by weight based on 100 parts by weight of the granules after the first coating treatment, i.e., first-coated granules, is preferred. Where the substance is used in too small an amount for forming a second coating or the mass to contain first-coated granules, first-coated granules cannot be sufficiently protected. Where the substance is used in too much an amount, protection of first-coated granules becomes excessive, and dissolution or swelling in the rumen of the substance for forming the second coating layer or the spherical, cubic or any other shaped mass is insufficient so that it is impossible to efficiently utilize the physiologically active substance as the core material in the abomasum and subsequent digestive tract.

Further, where first-coated granules are dispersed within a second coating material of a spherical or cubic shape, i.e., the second coating forms a spherical or cubic shape, the number of first-coated granules to be contained in the second coating is, as long as it is one or more, determined depending on the size of the spherical or cubic shape but is not particularly limited. In general, however, the size is preferably about 1 cm to about 5 cm from the view point of oral administration; and it is thus preferred for a sphere or cube of such size to contain 20 to 10000 first-coated granules having a diameter of about 0.4 mm to about 5 mm.

Upon the second coating, it is advantageous to use apparatuses for coating and granulating such as an apparatus for rolling granulation such as an apparatus for centrifugal flow granulation, an apparatus for fluid bed granulation, a drum type granulator, and a pan type granulation apparatus, a Marumerizer (Fuji Paudal Co., Ltd.), and an apparatus for stirring granulation. In order to obtain masses of a sphere, cubic or any other shape, composed of a second coating material and containing first-coated granules, a briquetting machine or a variety of other machines and apparatuses described in Handbook of Granulation, pages 83–399, edited by the Association of Japanese Powder Industry and published in 1975 by Omu Publishing Co.

Upon coating or granulation using these apparatuses, a binder is generally used for binding granules and a coating material. As the binder, substances having an adhesive property and allowed to use for food, feed, additives, drugs, etc. are used in the form of its aqueous solution or a solution in an organic solvent, and such solutions are applied by spraying.

In addition, dextrin, starch, gelatin or a glue coating material as such is dissolved or suspended in water and such solution or suspension is used as a binder.

There is no particular limitation to binders but there may be preferably used, for example, polyvinylpyrrolidone, hydroxypropyl cellulose, carboxymethyl cellulose, polyvinyl alcohol, dextrin, potato starch, etc.

Furthermore, clay, bentonite, gypsum, or the like which is not soluble but well dispersed in water may also be utilized.

The feed additives for ruminants of the present invention may further have a layer comprising a material which does not damage the requirements for feed additives, in addition to the first coating and the second coating described above.

EXAMPLES

Hereinafter the present invention is described in detail by referring to the examples.

In the following examples and comparative examples, "%" is all by weight unless otherwise indicated.

Evaluation as to whether or not feed additives are useful and practically usable for ruminants was made by the following criterion according to the following method.

Method 50 g of double coated granules or masses of a spherical, cubic or other shape and containing first-coated granules was blended with 500 g of corn silage. After allowing to stand at room temperature for 24 hours, the double coated granules or the masses containing first-coated granules were collected and evaluated by the following method.

In an Erlenmeyer flask having an inner volume of 1000 ml, 10 g of the granule or mass specimen was charged and 500 ml of McDougall's buffer([*1]) corresponding to the rumen juice in the rumen of a ruminant was added thereto. The flask was shaken in a thermostat of $39\pm0.5°$ C. at 91 times/min with an oscillation of 4 cm for 24 hours, and then the amount of the physiologically active substance dissolved out was quantitatively determined by high performance liquid chromatography.

(Notes) ([*1]): The McDougall's buffer is prepared by dissolving 7.43 g of sodium hydrogencarbonate, 7.0 g of disodium phosphate 12 hydrate, 0.34 g of sodium chloride, 0.43 g of potassium chloride, 0.10 g of magnesium chloride 6 hydrate and 0.05 g of calcium chloride in 1000 ml of water and saturating the solution with carbon dioxide gas (pH 6.8).

Next, the insoluble residue in the solution was collected by filtering through treble gauze sheets and washed into in the same flask as in the above with 500 ml of Clark-Lubs's buffer([*2]) corresponding to the gastric juice in the fourth stomach of a ruminant. The flask was shaken under the same conditions but for 3 hours, and then the amount of the physiologically active substance dissolved out was quantitatively determined by high performance liquid chromatography. (Notes)

([*1]): The McDougall's buffer is prepared by dissolving 7.43 g of sodium hydrogencarbonate, 7.0 g of disodium phosphate 12 hydrate, 0.34 g of sodium chloride, 0.43 g of potassium chloride, 0.10 g of magnesium chloride 6 hydrate and 0.05 g of calcium chloride in 1000 ml of water and saturating the solution with carbon dioxide gas (pH 6.8).

([*2]): The Clark-Lubs's buffer is prepared by adding 50 ml of 0.2N potassium chloride and 10.6 ml of 0.2N hydrochloric acid to 139.4 ml of water.

Criterion for Evaluation

When shaken for 24 hours in McDougall's buffer, at least 65%, desirably at least 75% of the physiologically active substance in the specimen was stably retained and most of the physiologically active substance in the specimen was dissolved out when shaken for 3 hours in Clark-Lubs's buffer, which was made the criterion for evaluation.

EXAMPLE 1

(a) Granulation of Core Material

In a granulating and coating apparatus by centrifugal flow (manufactured by Freund Industry Co., Ltd., CF- 360), 200 g of L-lysine hydrochloride crystals having a particle size of 20 to 24 mesh was charged as seed cores. While rolling, 2500 g of a 10:1 mixture of L-lysine hydrochloride and fine cellulose crystals (disintegrator) was gradually added in small portions and 1800 g of 4% aqueous solution of hydroxypropyl cellulose was sprayed as a binder, whereby granulation was carried out.

The obtained granules were dried with a fluid bed type dryer and classified through a standard sieve to obtain granules of 9 to 10 mesh and containing 89.2% of L-lysine hydrochloride.

The amino acid content of granule specimen was quantitatively determined by high performance liquid chromatography after dissolving 1 g of the specimen in 200 ml of Clark-Lubs's buffer. In the following examples and comparative examples, the amino acid content was quantitatively determined in the same fashion.

(b) First Coating

Ethanol was added to a copolymer of 4-vinylpyridine and styrene, a 1:1 by weight mixture of aluminum powder and talc powder, and stearic acid (weight ratio of 30:65:5) to achieve a copolymer concentration of 5%. The mixture was stirred at room temperature to prepare a slurry for coating.

800 g of the L-lysine hydrochloride granules obtained in (a) above was supplied into a flow coating apparatus (CF-360). While rolling, 4560 g of the slurry for coating was sprayed to form a coating layer. Thereafter, the coated granules were dried at 70° C. for 5 hours to give 994 g of granules with the first coating, i.e., first-coated granules. Calculation based on the weight increment, the ratio of the first coating layers to the whole granules was 19.5%.

The content of the L-lysine hydrochloride in 1 g of the thus obtained first-coated granules was 0.72 g. After shaking at 39° C. for 24 hours in McDougall's buffer, 98.1% of the L-lysine hydrochloride was retained in the granules. Further, by shaking at 39° C. for 2 hours and 3 hours in Clark-Lubs's buffer, 95% and 100% of the L-lysine hydrochloride were dissolved out, respectively.

(c) Second Coating

In a granulating and coating apparatus by centrifugal flow, 1000 g of the first-coated L-lysine hydrochloride granules obtained in (b) above was charged. While rolling, 700 g of dry-heated soybean powder (ground soybean powder) was gradually supplied as a second coating material in small portions, during which 800 g of 4% aqueous solution of hydroxypropyl cellulose was sprayed as a binder, whereby coating was carried out. The obtained granules were then dried with a fluid bed type dryer to obtain 1560 g of uniformly second-coated granules. Calculation based on the weight increment, the ratio of the second coating layer was 35.9%. The granules obtained by the second coating were almost spherical. When classified through a sieve of 8 mesh, the amount of the granules on the sieve was 15% based on the whole granules and most of the balance had a particle size of 8 to 9 mesh.

50 g of the thus obtained granules with the second coating, i.e., second-coated granules was blended with 500 g of corn silage, and some granules were collected as a specimen from the mixture 24 hours after. After shaking the specimen at 39° C. for 24 hours in McDougall's buffer, 98.1% of the L-lysine hydrochloride was retained without being dissolved out. Further, by shaking the insoluble residue at 39° C. for 3 hours in Clark-Lubs's buffer, 100% of the L-lysine hydrochloride was dissolved out.

COMPARATIVE EXAMPLE 1

50 g of the first-coated granules which were obtained in Example 1 (b) and contained 72% of L-lysine hydrochloride were directly blended with 500 g of corn silage as in Example 1 (c) without the second coating treatment with dry-heated soybean powder (ground soybean powder). Some granules were collected as a specimen 24 hours after. After shaking the specimen at 39° C. for 24 hours in McDougall's buffer, only 22.5% of the L-lysine hydrochloride was retained in the granules. Further, by shaking at 39° C. for 3 hours in Clark-Lubs's buffer the insoluble residue remaining after shaking in McDougall's buffer, the retained L-lysine hydrochloride was all dissolved out.

EXAMPLE 2

(a) Granulation of Core Material

Granules of L-lysine hydrochloride were obtained in a manner similar to Example 1 (a).

(b) First Coating 500 g of the granules obtained in (a) above was supplied into a flow coating apparatus. Using 3160 g of an ethanol slurry containing a copolymer of 4-vinylpyridine and styrene, a mixture of aluminum powder and talc powder, and stearic acid used in Example 1 (b), the first coating treatment was carried out. The ratio of the first coating layer was 21.2% of the total weight of the granules after coated.

The content of the L-lysine hydrochloride in 1 g of the thus obtained first-coated granules was 0.70 g. After shaking at 39° C. for 24 hours in McDougall's buffer, 100% of the L-lysine hydrochloride was retained. Further, by shaking at 39° C. for 3 hours in Clark-Lubs's buffer, 100% of the L-lysine hydrochloride was dissolved out.

(c) Second Coating

In a rolling granulation apparatus, 100 g of the first-coated L-lysine hydrochloride granules obtained in (b) above was charged. While rolling, 2000 g of heated soybean powder (ground soybean powder) was continuously supplied, during which 1000 ml of 5% aqueous solution of hydroxypropyl cellulose was sprayed, whereby spherical masses resulted. When the mass diameter became about 2 cm, the masses were sieved through sieves having a mesh of 2.0 cm and 2.6 cm. The masses passed through the sieves were returned to the apparatus to grow.

The thus obtained ball-like masses having a diameter of 2.0 to 2.6 cm were dried at 45° C. for 24 hours. The weight of one mass after drying was in a range of 4.2 to 9.2 g. Some masses were immersed in water to swell and then broken to count the number of the first-coated L-lysine hydrochloride granules contained in one mass. The number of the granules was in a range of 40 to 90.

50 g of the thus obtained ball-like masses was blended with 1000 g of corn silage (pH 4.2) and the blend was allowed to stand for 24 hours. The masses were collected and evaluated. As the result, 99.5% of the L-lysine hydrochloride in the specimen was retained after shaking at 39° C. for 24 hours in McDougall's buffer.

Further, by shaking at 39° C. for 3 hours in Clark-Lubs's buffer the insoluble residue remaining after shaking in McDougall buffer, 99.0% of the L-lysine hydrochloride was dissolved out.

EXAMPLE 3

(a) Granulation of Core Material

Granules of L-lysine hydrochloride were obtained in a manner similar to Example 1 (a).

(b) First Coating 400 g of the L-lysine hydrochloride granules obtained in (a) above were supplied into a flow coating apparatus. Using 2430 g of an ethanol slurry containing almost the same mixture (using no aluminum powder but using talc powder alone) as the coating material used in Example 1 (b), the first coating treatment was carried out. The ratio of the first coating layer was 20.5% of the total weight of the granules after coated.

The content of the L-lysine hydrochloride in 1 g of the thus obtained first-coated granules was 0.71 g. After shaking at 39° C. for 24 hours in McDougall's buffer, 100% of the L-lysine hydrochloride was retained. Further, by shaking at 39° C. for 3 hours in Clark-Lubs's buffer, 100% of the L-lysine hydrochloride was dissolved out.

(c) Second Coating

In a granulating and coating apparatus by centrifugal flow, 600 g of the first-coated L-lysine hydrochloride granules obtained in (b) above was charged. While rolling, 300 g of wheat powder which had passed through a sieve of 50 mesh was supplied to effect a second coating treatment, during which 470 g of 4% aqueous solution of hydroxypropyl cellulose was sprayed. Then the obtained granules were dried with a fluid bed type dryer to give 880 g of second-coated granules.

When calculated based on the weight increment, the ratio of the second coating layer to the whole granules was 31.8%. The granules obtained by the second coating were almost spherical. When classified through a sieve of 8 mesh, the amount of the granules on the sieve was 11% based on the whole granules and most of the balance had a particle size of 8 to 9 mesh.

50 g of the thus obtained granules second-coated with wheat powder was blended with 1000 g of corn silage (pH 4.2), the blend was allowed to stand for 24 hours, and then some granules were collected from the blend and subjected to evaluation. As the result, 98.0% of the L-lysine hydrochloride in the specimen was retained after shaking at 39° C. for 24 hours in McDougall's buffer. Further, by shaking at 39° C. for 3 hours in Clark-Lubs's buffer the insoluble residue remaining after shaking in McDougall's buffer, 98.0% of the L-lysine hydrochloride was dissolved out.

EXAMPLES 4 TO 7

First-coated L-lysine hydrochloride granules prepared as in Example 3 (a) and (b) were treated in a manner similar to Example 3 (c) to form a second coating layer, except for using casein, corn gluten meal, wheat gluten and corn powder instead of wheat powder.

The second-coated granules were almost spherical, and the granules in a range of 8 to 9 mesh amounted to 80 to 85% in any of the cases. The results are shown in Table 1.

TABLE 1

| | Example No. | 4 | 5 | 6 | 7 |
|---|---|---|---|---|---|
| L-lysine HCl granules | Amount charged (g) (L-lysine HCl content 0.71 g/1 g) | 600 | 600 | 600 | 600 |
| First coating layer | Ratio of coating layer (wt %) | 24.3 | 23.2 | 24.0 | 23.0 |
| Second coating layer | Kind of coating material | casein | corn gluten meal | wheat gluten | corn powder |
| | Amount charged (g) | 300 | 300 | 300 | 300 |
| | Ratio of coating layer (wt %) | 35.0 | 34.6 | 34.2 | 35.5 |
| Shaking test | Time for standing of blend with corn silage (hr) | 24 | 24 | 24 | 24 |
| | Retention rate (%) of lysine in McDougall's buffer (pH 6.8, 24 hrs) | 98.0 | 98.5 | 97.6 | 98.2 |
| | Dissolution rate (%) of lysine in Clark-Lubs buffer (pH 2.0, 3 hrs) | 100 | 100 | 100 | 100 |

EXAMPLES 8 TO 12

First-coated L-lysine hydrochloride granules prepared as in Example 2 (a) and (b), materials for forming a second coating layer, a binder and water in ratios as shown in Table 2 were treated to prepare a mixture for molding. The mixture was molded with a briquetting machine to give a ball-like mass product containing a plurality of the granules.

After drying, efficiency was evaluated and the results are shown in Table 2.

○ Uniform blending of raw materials

In an all-purpose mixer of planetarium type which can uniformly blend raw materials by round-the-sun-and-on-its-axis revolution of vanes were charged (1) the first coated granules described above, (2) materials for forming a second coating layer (talc, corn zein, crystalline cellulose) and (3) binder (hydroxypropyl cellulose, polyvinylpyrrolidone). By thoroughly stirring, the raw materials were blended with each other. When the materials were blended almost uniformly, the blend was stirred while adding water in small portions. Water was added up to the volumes described in Table 2 to impart suitable moisture and binding property required for molding.

○ Molding

The uniformly blended materials described above were charged in a briquetting machine and compressed for molding to give ball-like mass product. The ball-like masses were dried with hot air at 60° C. for 10 hours to give the molded masses having a strength sufficient to cause no damage by blending procedures with feed.

TABLE 2

| | Example No. | | | | |
|---|---|---|---|---|---|
| | 8 | 9 | 10 | 11 | 12 |
| Composition of raw materials (g): | | | | | |
| First coated granules | 550 | 300 | 300 | 300 | 600 |
| Talc | 550 | 500 | | | 300 |
| Corn zein | | 300 | | | |
| Fine crystalline | | | 600 | 300 | 100 |

TABLE 2-continued

| | Example No. | | | | |
|---|---|---|---|---|---|
| | 8 | 9 | 10 | 11 | 12 |
| cellulose *1) | | | | | |
| Hydroxypropyl cellulose *2) | | 20 | | | |
| Polyvinyl-pyrrolidone *3) | 30 | | 10 | 10 | 5 |
| Subtotal | 1130 | 1120 | 910 | 610 | 1105 |
| Water | 400 | 700 | 800 | 460 | 300 |
| Weight of one briquet (g) | 9 | 8.5 | 7.5 | 7.5 | 8.2 |
| Mean number of first coated granules in one briquet | 1095 | 569 | 618 | 912 | 1212 |
| Shaking test: | | | | | |
| Time for standing of blend with corn silage (hrs) | 24 | 24 | 24 | 24 | 24 |
| Retention rate (%) of lysine in McDougall's buffer (pH 6.8, 24 hrs) | 98.0 | 98.0 | 98.5 | 98.0 | 97.5 |
| Dissolution rate (%) of lysine in Clark-Lub's buffer (pH 2.0, 3 hrs) | 100 | 100 | 100 | 100 | 100 |

Notes:
*1) manufactured by Asahi Chemical Industry Co., Ltd., AVICEL, pH 102
*2) manufactured by Nippon Soda Mfg. Co., Ltd. HPC-L
*3) manufactured by BASF Co., Ltd., PVP (K-90)

EXAMPLE 13

(a) Granulation of Core Material

Into a granulating and coating apparatus by centrifugal flow (CF-360) was introduced 200 g of L-lysine hydrochloride crystals having a particle size of 20 to 24 mesh as seed cores. While rolling, a mixture of 2100 g of L-lysine hydrochloride and 300 g of talc was added little by little, during which 1800 g of a water-methanol (40:60) solution containing 3% of polyvinylpyrrolidone (K-90) was sprayed as a binder, whereby granulation was carried out. The obtained granules were dried in a fluid bed type drier and then classified through a JIS standard sieve to obtain granules of 9 to 10 mesh.

To a CF-360 was supplied 700 g of these granules, and while spraying a 3% water-ethanol solution (water:ethanol =40:60) of polyvinylpyrrolidone, 90 g of talc was supplied little by little to perform coating, followed by drying in a fluid bed type drier. Further, the dried granules were classified through a JIS standard sieve to obtain granules coated uniformly with talc and having a good surface smoothness. The content of the L-lysine hydrochloride contained in the granules thus obtained was 76.0%.

(b) First Coating

Methanol was added to a mixture (70:30) of talc powder and a copolymer (reduced viscosity at a concentration of 0.5 g/dl in ethanol: η sp/c=1.30) of 4-vinylpyridine (70 wt %)-styrene (30 wt %) so that the concentration of the copolymer was 5%, and then, the mixture was stirred at room temperature to prepare a coating slurry.

700 g of the granules which were obtained in (a) above and had a layer consisting primarily of talc on the surface was supplied to a CF-360, and while rolling the granules, the above coating slurry was sprayed thereon to perform coating so that the ratio of the coating layer of the coated granules was 26% by weight, which was calculated based on the increase in weight after drying.

The content of the L-lysine hydrochloride in the first coated granules thus obtained was 0.56 g/g of the granules, and 98% thereof was retained after shaking at 90° C. for 24 hours in a McDougall's buffer. Further, shaking at 39° C. for 3 hours in a Clark-Lubs's buffer dissolved 95% of the L lysine hydrochloride.

(c) Second Coating

Into a rolling granulation apparatus was charged 100 g of the first-coated L-lysine hydrochloride granules obtained in (b) above. While rolling the granules and spraying thereon a 3 wt % aqueous solution of polyvinylpyrrolidone, 2000 g of heated soybean powder was continuously supplied to grow the granules to balls. When the diameter of the balls became about 2 cm, they were classified through sieves having a mesh of 2.0 cm and 2.6 cm to collect balls having a size falling within this range. Then, the classified balls were dried to obtain the objective balls.

The balls thus obtained were evaluated in the same manner as in Example 3 (c). The retaining test performed by shaking in a McDougall's buffer and the dissolving-out test performed by shaking in the Clark-Lubs's buffer gave the excellent results of more than 90%, respectively.

EXAMPLE 14

(a) Granulation of Core Material

Into a granulating and coating apparatus by centrifugal flow (CF-360) was introduced 200 g of L-lysine hydrochloride crystals having a particle size of 20 to 24 mesh as seed cores. While rolling, a mixture of 2200 g of L-lysine hydrochloride and 300 g of kaolin was added little by little, during which 1800 g of a 4% water-ethanol (water:ethanol=40:60) solution of hydroxypropyl cellulose were sprayed as a binder, whereby granulation was performed. The obtained granules were dried in a fluid bed type drier and then classified through a JIS standard sieve to obtain granules of 9 to 10 mesh.

To a CF-360 was supplied 700 g of these granules, and while spraying a 3% aqueous solution of hydroxypropyl cellulose, 90 g of fine powder of kaolin was supplied little by little to perform coating, followed by drying in a fluid bed type drier. Further, the dried granules were classified through a JIS standard sieve to obtain granules coated uniformly with kaolin and having a good surface smoothness. The content of the L-lysine hydrochloride in the granules thus obtained was 75.0%.

(b) First Coating

Ethanol was added to a mixture (70:30) of talc powder and a copolymer (reduced viscosity at a concentration of 0.5 g/dl in ethanol: η sp/c=0.70) of 2-vinylpyridine (70 wt %)-styrene (30 wt %) so that the concentration of the copolymer was 5%, and then, the mixture was stirred at room temperature to prepare a coating slurry.

700 g of the granules obtained in (a) above was supplied to a CF-360, and while rolling the granules, the above coating slurry was sprayed thereon to perform coating so that the ratio of the coating layer of the coated granules was 25% by weight, which was calculated based on the increase in weight after drying.

The first-coated granules thus prepared had a L-lysine hydrochloride content of 0.56 g/g of the granules, and 96% thereof was retained after shaking at 39°

C. for 24 hours in a McDougall's buffer. Further, shaking at 39° C. for 3 hours in a Clark-Lubs's buffer dissolved out 96% of the L-lysine hydrochloride.

(c) Second Coating

Into a rolling granulation apparatus was charged 100 g of the first-coated L-lysine hydrochloride granules obtained in (b) above. While rolling the granules and spraying thereon a 4 wt % aqueous solution of hydroxypropyl cellulose, 2000 g of heated soybean powder was continuously supplied to grow the granules to balls. When the diameter of the balls became about 2 cm, they were classified through sieves of 2.0 cm and 2.6 cm. Then, balls having a size falling within this range were dried to obtain the objective balls.

The balls thus obtained were evaluated in the same manner as in Example 3 (c). The retaining test performed by shaking in the McDougall's buffer and the dissolving-out test performed by shaking in the Clark-Lubs's buffer gave excellent results of more than 90%, respectively.

EXAMPLE 15

(a) Granulation of Core Material

Into a granulating and coating apparatus by centrifugal flow (CF-360) was introduced 350 g of white sugar having a particle size of 20 to 24 mesh as seed cores. While rolling, a mixture of 1500 g of L-lysine hydrochloride 500 g of D,L-methionine and 300 g of talc was added little by little, during which 900 g of a 4% water-methanol (water:methanol=40:60) solution of hydroxypropyl cellulose was sprayed as a binder, whereby granulation was performed. The obtained granules were dried in a fluid bed type drier and then classified through a JIS standard sieve to obtain granules of 9 to 10 mesh.

To a CF-360 was supplied 700 g of the granules thus obtained, and while spraying a 4% water-methanol solution (water:methanol=40:60) of hydroxypropyl cellulose, 90 g of talc powder was supplied little by little to perform coating, followed by drying in a fluid bed type drier. Further, the dried granules were classified through a JIS standard sieve to obtain granules coated uniformly with talc and having a good surface smoothness. The contents of the L-lysine hydrochloride and the D,L-methionine in the granules thus obtained were 48.4% and 16.1%, respectively.

(b) First Coating

Methanol was added to a mixture (70:30) of talc powder and a copolymer (reduced viscosity at a concentration of 0.5 g/dl in ethanol: $\eta$ sp/c=1.30) of 4-vinylpyridine (70 wt %)-styrene (30 wt %) so that the concentration of the copolymer was 5%, and then, the mixture was stirred at room temperature to prepare a coating slurry.

700 g of the granules obtained in (a) above was supplied to a CF-360, and while rolling the granules, the above coating slurry was sprayed thereon to perform coating so that the ratio of the coating layer of the coated granules was 26% by weight, which was calculated based on the increase in weight after drying.

The contents of the L-lysine hydrochloride and the D,L-methionine in the first-coated granules thus obtained were 0.36 g and 0.12 g/g of the grain, respectively, and 97% of the amino acids was retained after shaking at 39° C. for 25 hours in a McDougall's buffer. Further, shaking at 39° C. for 3 hours in a Clark-Lubs's buffer dissolved out 94% of the amino acids in the granules.

(c) Second Coating

Into a rolling granulation apparatus was charged 100 g of the first-coated amino acid mixture granules obtained in (b) above. While rolling the granules and spraying thereon a 4 wt % aqueous solution of hydroxypropyl cellulose, 2000 g of heated soybean powder was continuously supplied to grow the granules to balls. When the diameter of the balls became about 2 cm, they were classified through sieves having a mesh of 2.0 cm and 2.6 cm. Then, balls having a size falling within this range were dried to obtain the objective balls.

The balls thus obtained were evaluated in the same manner as in Example 3 (c). The retaining test of the amino acids performed by shaking in a McDougall's buffer and the dissolving-out test of the amino acids performed by shaking in a Clark-Lubs's buffer gave excellent results of more than 90%, respectively.

What is claimed is:

1. A feed additive granule comprising at least one granulated physiologically active substance selected from the group consisting of nutrients, feeds containing the same and medicines, said granulated physiologically active substance being coated with a first coating layer, said first coating layer comprising a polymer selected from the group consisting of:

(a) cellulose derivatives containing amino groups, basic nitrogen atoms or both;

(b) a polyvinylpyridine, polyvinyldiethylaminoacetoacetal, polyvinylbenzylaminoacetoacetal, polyvinylacetal diethylaminoacetate, polydiethylaminomethylstyrene, polydiethylaminomethylstyrene, polydimethylaminoethyl methacrylate;

(c) copolymers of a monomer having an amino group or basic nitrogen atom selected from the group consisting of a vinylpyridine, dimethylaminoethyl methacrylate, N,N-diethylvinylamine, vinylpiperazine, vinylbenzylamine, vinylpiperidylacetoacetal, dimethylaminoethyl acrylate, 2-(4-morpholino)ethylacrylate, N,N-dimethylaminopropylacrylamide, N,N-dimethylaminopropylmethacrylamide, a vinylethylpyridine, 2-methyl-5-vinylpyridine and 2-methyl-6-vinylpyridine, with one or more copolymerizable monomers selected from the group consisting of alkyl methacrylates, alkyl acrylates, vinyl acetate, styrene, acrylonitrile and butadiene;

(d) a condensation reaction product of terephthalic acid or maleic acid with N-n-butyldiethanolamine; and (e) a benzylamine adduct of a propylene glycol/maleic acid polyester, wherein said polymer of said first coating layer dissolves or swells in water having a pH of not greater than 5.5 and is stable in a pH of 5.6 to 8.0, said granulated physiologically active substance coated with said first coating layer being coated with a second coating layer selected from the group consisting of ground cereals, ground beans, ground potatoes, vegetable oil lees, brans, processed lees, animal product feeds, yeasts, sugars, vegetable protein, crystalline cellulose, talc, silica, white mica, vitamins and mixtures thereof, wherein said second coating layer is acceptable to ruminants, is stable in water having a pH of not greater than 5.5 and which dissolves or swells at a pH of 5.6 to 8.0, said first coating layer being present in an amount of from 10 to 200 wt % based on the weight of said granulated physiologically active substance, and said second coating layer being present in an amount of from 2 to 200 parts by weight based on 100 parts by weight of said granulated physiologically active substance coated with said first coating layer.

2. The granule of claim 1, wherein said polyvinylpyridine is selected from the group consisting of poly(2-methyl-5-vinylpyridine), poly(2-ethyl-5-vinylpyridine), poly(2-vinylpyridine) and poly(4-vinylpyridine).

3. The granule of claim 1, wherein said vinylpyridine is 2-vinylpyridine or 4-vinylpyridine.

4. The granule of claim 1, wherein said copolymer is selected from the group consisting of a 2-vinylpyridine/styrene copolymer, a 4-vinylpyridine/styrene copolymer, a 2-methyl-5-vinylpyridine/styrene copolymer, and a 2-ethyl-5-vinylpyridine/styrene copolymer.

* * * * *